US007862515B2

(12) United States Patent  (10) Patent No.: US 7,862,515 B2
de Chazal et al.  (45) Date of Patent: *Jan. 4, 2011

(54) APPARATUS FOR DETECTING SLEEP APNEA USING ELECTROCARDIOGRAM SIGNALS

(75) Inventors: Philip de Chazal, Sutton (AU); Conor Heneghan, Dublin (IE); Elaine Sheridan, County Cavan (IE)

(73) Assignee: Biancamed Limited, Dublin (IE)

( * ) Notice: Subject to any disclaimer, the term of this patent is extended or adjusted under 35 U.S.C. 154(b) by 1243 days.

This patent is subject to a terminal disclaimer.

(21) Appl. No.: 11/308,429

(22) Filed: Mar. 24, 2006

(65) Prior Publication Data

US 2006/0184056 A1  Aug. 17, 2006

Related U.S. Application Data

(63) Continuation of application No. 09/952,688, filed on Sep. 14, 2001, now Pat. No. 7,025,729.

(51) Int. Cl.
*A61B 5/0402* (2006.01)
(52) U.S. Cl. ..................................................... 600/508
(58) Field of Classification Search .......... 600/508–519
See application file for complete search history.

(56) References Cited

U.S. PATENT DOCUMENTS

| 4,129,125 | A | 12/1978 | Lester |
| 4,306,567 | A | 12/1981 | Krasner |
| 4,715,367 | A | 12/1987 | Crossley |
| 4,982,738 | A | 1/1991 | Griebel |
| 5,105,354 | A | 4/1992 | Nishimura |
| 5,275,159 | A | 1/1994 | Griebel |

(Continued)

FOREIGN PATENT DOCUMENTS

EP  1 146 433 A1  10/2001

(Continued)

OTHER PUBLICATIONS

Cyclical Variation of the Heart Rate in Sleep Apnoea Syndroms: Mechanisms, and Usefulness of 24 h Electrocardiography as a Screening Technique, Guillemlnault, C.; Connolly, S.; Winkle, R.; Melvin, K.; Tilkian, A., Lancet, Jan. 21, 1984; 1(8369): 126-31.

(Continued)

*Primary Examiner*—George R Evanisko
(74) *Attorney, Agent, or Firm*—Pillsbury Winthrop Shaw Pittman LLP

(57) ABSTRACT

An apparatus for diagnosing sleep apnea only uses an electrocardiogram signal and a computer processor and associated computer code that are configured to analyze the electrocardiogram signal and classify each time period of the electrocardiogram signal as either apneic or normal. A diagnostic measure of sleep apnea for the human patient is provided based on classification results obtained by combining a results for various electrocardiogram signal time periods. A computer-readable medium has computer code that causes the computer to analyze an electrocardiogram signal relating to the human patient and classify each time period in a set of time periods as either apneic or normal. A diagnostic measure of sleep apnea is provided based on classification results obtained by combining a plurality of results from the set of time periods using either time or frequency domain processing, or both.

9 Claims, 9 Drawing Sheets

U.S. PATENT DOCUMENTS

| | | | |
|---|---|---|---|
| 5,291,400 | A | 3/1994 | Gilham |
| 5,765,563 | A | 6/1998 | Vander Schaaf |
| 5,769,084 | A | 6/1998 | Katz |
| 5,797,852 | A | 8/1998 | Karakasoglu |
| 5,891,023 | A | 4/1999 | Lynn |
| 5,902,250 | A | 5/1999 | Verrier et al. |
| 6,062,216 | A | 5/2000 | Corn |
| 6,091,973 | A | 7/2000 | Colla |
| 6,142,950 | A | 11/2000 | Allen |
| 6,415,174 | B1 | 7/2002 | Behbehani |
| 7,025,729 | B2 * | 4/2006 | de Chazal et al. ........... 600/508 |

FOREIGN PATENT DOCUMENTS

| | | |
|---|---|---|
| GB | 2214302 | 8/1989 |
| JP | 05-200001 | 8/1993 |
| WO | WO-99/34864 | 7/1999 |

OTHER PUBLICATIONS

Derivation of Respiratory Signals from Multi-lead ECGs, George B. Moody, Roger G. Mark, Andrea Zoccola, and Sara Mantero, Computers in Cardiology 1985, vol. 12, pp. 113-116 (Washington, DC: IEEE Computer Society Press).

Clinical Validation of the ECG-Derived Respiration (EDR) Technique, George B. Moody, Roger G. Mark, Marjorie A. Bump, Joseph S. Weinstein, Aaron D. Berman, Joseph E. Mietus, and Ary L. Goldberger, Computers in Cardiology 1986, vol. 13, pp. 507-510 (Washington, DC: IEEE Computer Society Press).

Detection of Obstructive Sleep Apnea from Cardiac Interbeat Interval Times Series, JE Mietus, C-K Peng, PCh Ivanov, AL Goldberger, Computers in Cardiology 2000, vol. 27, pp. 753-756 (Piscataway, NJ: The Institute of Electrical and Electronics Engineers, Inc.).

Spectral Indices of Cardiac Autonomic Function in Obstructive Sleep Apnea, Michael C.K. Khoo. Tae-Sun Kim, and Richard B. Berry, SLEEP, vol. 22, No. 4, 1999.

"Automated Processing of the Single-Lead Electrocardiogram for the Detection of Obstructive Sleep Apnoea", Philip de Chazal et al., IEEE Transactions on Biomedical Engineering, vol. 50, No. 6, Jun. 2003, pp. 686-696.

"Automatic Classification of Sleep Apnea Epochs using the Electrocardiogram", P. de Chazal et al., IEEE Computers in Cardiology 2000; 27: pp. 745-748 (Conference paper presented Sep. 24-27, 2000 in Cambridge, MA).

\* cited by examiner

APPARATUS FOR DETECTING SLEEP APNEA USING ELECTROCARDIOGRAM SIGNALS

CROSS REFERENCE TO RELATED APPLICATIONS

This application is a Continuation under 35 U.S.C. §120 of application Ser. No. 09/952,688 filed on Sep. 14, 2001, the entire contents of which are incorporated herein by reference.

BACKGROUND

This disclosure relates to cardio-respiratory monitoring and analysis, and more particularly to methods for diagnosing sleep disorders. More specifically, this disclosure is aimed at detection of sleep apnea using the electrocardiogram. The invention can be embodied in a form suitable for use in a dedicated medical setting, or in the home.

Sleep apnea is a significant public health problem. Current estimates are that approximately 4% of the male middle-aged population, and 2% of the female middle-aged population suffer from sleep apnea. Patients suffering from sleep apnea are more prone to hypertension, heart disease, stroke, and irregular heart rhythms. Continued interruption of quality sleep is also associated with depression, irritability, loss of memory, lack of energy, and a higher risk of car and workplace accidents.

Current techniques for detection and diagnosis of sleep apnea rely upon hospital-based polysomnography. A polysomnogram simultaneously records multiple physiologic signals from the sleeping patient. A typical polysomnogram includes measurements of blood oxygen saturation level, blood pressure, electroencephalogram, electrocardiogram, electrooculogram, electromyogram, nasal and/or oral airflow chest effort, and abdominal effort. Typically, signals are recorded from a full night's sleep and then a diagnosis is reached following a clinical review of recorded signals. In some patients a second night's recording is required. Because of the number and variety of measurements made, this test can be uncomfortable for the patient and also has a relatively high cost. In general, it is only performed in a dedicated medical facility.

A variety of techniques have been proposed for simpler systems to detect sleep apnea. Acoustic screening devices have been proposed which detect loud snoring, or which detect long periods of silence which may indicate a dangerously long acute sleep apnea episode.

These are disclosed in U.S. Pat. No. 4,715,367. Other acoustic-based devices are disclosed in U.S. Pat. Nos. 5,797, 852, 4,306,567, 4,129,125, and United Kingdom Patent Specification No. 2,214,302.

Detection systems using only measurements of respiratory effort or flow have also been disclosed. U.S. Pat. No. 6,062, 216 discloses the use of a light beam to detect breathing motion. U.S. Pat. No. 6,142,950 uses an airflow sensor attached to the upper lip to detect inspiration and expiration airflow. WO 99/34864 discloses a nasal thermistor which responds to changes in nasal airflow and hence provides assessment of apnea.

A variety of detection systems have been disclosed which use combinations of measurements to detect sleep apnea. U.S. Pat. No. 6,091,973 uses measurements of skin conductance, heart rate, and blood oxygen saturation to detect arousals from apnea or hypopnea. U.S. Pat. No. 5,769,084 relies on processing of combinations of nasal air-flow, chest wall effort, oxygen saturation, heart rate, and heart activity in order to identify the onset and duration of breathing disorder. U.S. Pat. No. 5,765,563 discloses a system for using measurements of airflow, heart rate, and oxygen saturation for detection of apnea, hypopnea, and oxygen desaturation. U.S. Pat. No. 5,275,159 discloses a system which combines heart rate, respiratory and snoring sounds, oxygen saturation, and bodily position to detect apnea. U.S. Pat. No. 5,105,354 discloses a system for combining respiration and heart rate to detect sleep apnea in infants. U.S. Pat. No. 4,982,738 discloses a system which combines heart rate, respiratory and snoring sounds to detect apnea. U.S. Pat. No. 5,291,400 incorporates a system for the analysis of heart rate variability, but not in relation to the detection of sleep apnea.

Japanese Patent Specification No. JP 5,200,001 discloses a technique for measuring chest wall motion and hence detecting apnea. U.S. Pat. No. 5,891,023 discloses a technique for using desaturation and resaturation events in oxygen saturation.

Disadvantages of solutions based on the prior art include a high level of complexity due to the number of measurements required, and/or relatively low levels of accuracy in correctly diagnosing sleep apnea. The present invention seeks to overcome the aforementioned disadvantages associated with the prior art Review of Electrocardiogram Terminology The Electrocardiogram:

The heart is a muscular organ containing four chambers. The two smallest chambers are the left and right atria and the two largest chambers are left and right ventricles. The heart alternatively contracts and relaxes at the rate of approximately once per second as it pumps blood around the body. During this cycle (or beat) there are changes to the electrical charge surrounding the heart cells that result in potential gradients on the body surface. Any two electrodes placed on the body surface can measure these potential gradients. The electrocardiogram signal is a plot of these body surface potential differences against time. Thus, the electrocardiogram is a non-invasive technique for measuring the electrical activity (or cardiac potentials) of the heart.

Normal Electrocardiogram

The normal electrocardiogram has a number of characteristic patterns associated with each beat of the heart: the P wave, the QRS complex and the T wave. A number of measurements are routinely measured from the electrocardiogram relating to various inter- and intra-beat characteristics. An example of an inter-beat measurement is the time duration between each R wave peak of the QRS complex, referred to herein as the RR interval. Examples of intra-beat measurements include PR and QT intervals. A typical electrocardiogram signal obtained from a standard lead configuration is shown in FIG. 1 and consists of the three standard waveform components. The PR interval and the QT interval are identified on FIG. 1 as well as the PR segment and the ST segment. The letters do not have physiologic significance but the corresponding waves do as they relate to the electrical activity in specific regions of the heart.

P Wave:

During a beat of the heart the first event normally visible on the electrocardiogram is the P wave. The P wave occurs as a result of the electrical activity associated with the contraction of the two atria. In some electrocardiograms the P wave may not be visible. The normal duration of the P wave is 0 (no visible P wave) to 100 ms, measured from the onset to the offset of the P wave.

QRS Complex:

The next event apparent on the electrocardiogram is the QRS complex, which results from the electrical activity associated with contraction of the two ventricles. A normal QRS complex is generally comprised of a Q wave, an R wave and an S wave. Every positive deflection in this complex is called an R wave. The first negative deflection prior to the R wave is termed a Q wave and the first negative deflection following the R wave is called an S wave. Second and third positive deflections are possible and are called an R' wave and an R'' wave respectively. The initial part of the QRS complex is related to the activity of both ventricles and the latter part is principally the left ventricle. The QRS complex is a much larger signal than the P wave for two reasons. Firstly, the ventricles are closer to the chest surface than the atria and secondly the ventricles contain much more tissue than the atria.

The QRS duration is measured from the start of the Q wave to the end of the S wave. It represents the amount of time needed for ventricular depolarization and its normal duration is 50-100 ms.

T Wave:

The last major event of the electrocardiogram it the T wave and it corresponds to the electrical activity associated with the ventricles relaxing. The normal T wave duration is typically between 100-250 ms. The atria also have a relaxation phase. This is not visible on the electrocardiogram as it occurs at the same time as the much larger QRS complex.

SUMMARY

This disclosure provides diagnostic recording apparatus including means for measuring cardiac potentials from the skin. The apparatus of the invention also includes signal processing techniques to filter out unwanted interference due to motion artifact, electromyograms, power line noise, and baseline wander. It incorporates means for recording both the unprocessed and processed cardiac potential signals. This diagnostic recording apparatus is capable of communicating with external devices (e.g., computer, mobile communication terminal, stand-alone console) using either direct physical connection or wireless connection. In an alternative embodiment, the apparatus may incorporate its own display interface that allows direct inspection of the analysis results.

Accordingly, this disclosure provides a diagnostic recording apparatus comprising: means for measuring cardiac electrical potential from a human for generating an electrocardiogram signal; means for analyzing said electrocardiogram signal to produce an output signal; and means for providing a diagnostic measure of sleep apnea based on said output signal.

The apparatus may include signal processing means for filtering out unwanted interference from the electrocardiogram signal and for producing a processed electrocardiogram signal for inputting to the analyzing means.

The apparatus may also include means for recording the processed electrocardiogram signal.

The means for analyzing said processed electrocardiogram signal may comprise a computer algorithm performed within said apparatus. Alternatively, said means may comprise a computer algorithm performed on an external device, and the apparatus includes means for communicating with said device. Preferably, the apparatus includes a display interface which allows direct inspection of the analysis results.

Only a single channel of electrocardiogram signal may be analyzed. Alternatively, a multichannel signal may be employed.

In one arrangement the apparatus includes; means for calculating the RR time interval between successive QRS complexes from the electrocardiogram signal; means for isolating an electrocardiogram-derived respiratory signal; and means for obtaining measurements from the RR intervals and electrocardiogram-derived respiratory signal to provide a diagnostic measure.

In a second aspect, this disclosure provides a method of obtaining a diagnostic measure of sleep apnea, the method comprising a. acquiring single-channel or multi-channel electrocardiogram signal from a human over a period of time; b. filtering the signal to remove electrical interference; c. calculating a sequence of RR intervals from the electrocardiogram signal by measuring the time interval between successive QRS complexes; d. obtaining an electrocardiogram-derived respiratory signal; e. partitioning the electrocardiogram signal into a set of shorter time periods; f. obtaining measurements from the sequence of RR intervals and the electrocardiogram-derived respiratory signal for each time period; g. for each time period, calculating the probability that it can be classified as apneic or normal by processing the measurements for that time period using a classifier model which has been trained on a pre-existing database of signals; and h. combining probabilities for each time period to provide an overall diagnostic measure.

The measurements in step (f) may be selected from the group consisting of: I. the power spectral density of the electrocardiogram-derived respiratory signal; II. the mean and standard deviation of the electrocardiogram-derived respiratory signal; III. the power spectral density of the RR intervals; IV. the mean and standard deviation of the RR intervals; V. the first five serial correlation coefficients of the RR intervals; VI. the Allan factor A(T) evaluated at a time scale T of 5, 10, 15, 20 and 25 seconds where the Allan factor is defined as $$A(T) = \frac{E\{[N_{i+1}(T) - N_i(T)]^2\}}{2E\{N_{i+1}(T)\}},$$

where $N_i(T)$ is the number of R wave peaks occurring in a window of length T stretching from iT to (i+1)T, and E is the expectation operator; VII. the NN50 measure (variant 1), defined as number of pairs of adjacent RR intervals where the first interval exceeds the second interval by more than 50 ms; VIII. the NN50 measure (variant 2), defined as number of pairs of adjacent RR intervals where the second interval exceeds the first interval by more than 50 ms; IX. two pNN50 measures, defined as each NN50 measure divided by the total number of RR intervals X. the SDSD measures, defined as the standard deviation of the differences between adjacent RR intervals, and XI. the RMSSD measure defined as the square root of the mean of the sum of the squares of differences between adjacent RR intervals; XII. the mean or standard deviation of the RR signal over the entire recorded electrocardiogram; and XIII. the mean or standard deviation of the electrocardiogram-derived respiratory signal over the entire recorded electrocardiogram.

In step (c) the RR interval sequence is obtained by first identifying QRS complexes in the electrocardiogram signal and determining the times of occurrences of the R-wave peak in the QRS complexes thereby providing a series of times at which the R-wave peaks occur. The sequence of RR intervals is then obtained by measuring the time interval between successive R-wave peaks.

The electrocardiogram-derived respiratory signal in step (d) is obtained by extracting QRS complexes in the electrocardiogram signal and determining the times of occurrences of the R-wave peak in the QRS complexes and by taking the locations of the R-wave peaks and calculating the area represented by the signal near said locations. After step (g), the method further includes the step of recalculating the probability of a given time period containing an apneic episode using the probabilities generated for neighboring time periods calculated in step (g).

The method includes the step of converting the diagnostic measure to a Apnea-Hyponea Index or Respiratory Disturbance Index.

In one arrangement, after step (b), the method also includes determining whether the electrocardiogram signal is suitable for proceeding to carrying out the analysis; and indicating if the electrocardiogram signal is deemed unsuitable following said determination step.

The power spectral density of the electrocardiogram-derived respiratory signal is calculated using an averaged periodogram technique. The power spectral density of the RR intervals is calculated using an averaged periodogram technique The classifier model may be selected from the group consisting of: (1) a linear discriminant classifier; (2) a quadratic discriminant classifier; and (3) a regularized quadratic discriminant classifier.

According to yet another aspect, this disclosure provides a system for providing a diagnostic measure for sleep apnea including a diagnostic recording apparatus including means for measuring cardiac potentials from a human to generate an unprocessed electrocardiogram signal; means for processing the unprocessed electrocardiogram signal and extracting RR intervals and an electrocardiogram-derived respiratory signal from the unprocessed electrocardiogram signal, where RR intervals are defined as the time durations between successive QRS complexes in the electrocardiogram signal; means for dividing the electrocardiogram signal into time periods; means for identifying time periods as containing apneic episodes and time periods not containing apneic episodes; means for providing reports which indicate apneic periods, non-apneic periods and indeterminate periods, and for correlating these events with the electrocardiogram signal; and means for providing an overall diagnostic measure in a clinically meaningful form based on the reports.

Means are provided for correlating the apneic, non-apneic and indeterminate periods with the electrocardiogram signal using a visual representation.

According to yet a further aspect, this disclosure provides a method of obtaining a diagnostic measure of sleep apnea, comprising measuring cardiac electrical potential from the skin of a patient; generating an electrocardiogram signal from the measured potential; analyzing the electrocardiogram signal to produce an output signal; and providing a diagnostic measure of sleep apnea based on said output signal.

Conveniently, the method includes processing the electrocardiogram signal to filter out unwanted interference therefrom and analysing the processed signal. The diagnostic summary is provided in units of apneic minutes/hour, Apnea-Hypopnea Index, or other such clinically meaningful form.

A method of diagnosing sleep apnea includes computing measurements based on the RR interval power spectral density, the electrocardiogram-derived respiratory signal power spectral density, the mean and standard deviation of the RR signal and the electrocardiogram-derived respiratory signal, and a range of time-domain measurements of RR variability. These measurements are processed by a classifier which has been trained on a pre-existing data base of electrocardiogram signals, and which provides a probability of a specific time period containing apneic episodes. The probability for a number of time periods can be combined to form the overall diagnostic summary for a patient.

Thus, the present invention provides a diagnostic recording apparatus comprising means for measuring cardiac electrical potentials from human skin, signal processing techniques for filtering out unwanted interference, giving a processed cardiac potential signal, means for recording either or both the unprocessed and processed cardiac potential signals, means for analyzing said cardiac potential signals and means for providing a diagnosis of sleep apnea using only said electrocardiogram signal.

One aspect of the apparatus may include means for communicating with external devices for analyzing the recorded electrocardiogram signal.

Ideally, the means for analyzing said recorded cardiac potential signal comprises a computer algorithm performed on a computer located remotely from the diagnostic recording apparatus. The apparatus may communicate with the computer via wireless or wire connection.

Advantageously, the means for analyzing said recorded cardiac potential signal comprises a computer algorithm performed within said apparatus so that the apparatus comprises means for recording the electrocardiogram signal and means for carrying out analysis of said sleep apnea using only a single channel of electrocardiogram signal.

In another aspect, the apparatus includes means for calculating intervals between R wave peaks on the electrocardiogram signal, thereby providing a sequence of RR intervals and means for isolating an electrocardiogram-derived respiratory signal. Means are provided for using spectral measures derived from the RR intervals and electrocardiogram-derived respiratory signal.

In one arrangement, the recording apparatus includes its own display interface which allows direct inspection of the analysis results.

The method may include the step of incorporating additional processing of the classifications of neighboring time periods to increase the accuracy of a given time period.

In one aspect, the method may include converting the diagnosis on a per-minute basis to the Apnea-Hyponea index or Respiratory Disturbance Index.

The electrocardiogram-derived respiratory signal may be calculated by taking the locations of the R-wave peaks and calculating the area enclosed by the signal near said locations.

The power spectral densities of the RR intervals and the electrocardiogram-derived respiratory signal may be calculated using an averaged periodogram technique.

BRIEF DESCRIPTION OF THE DRAWINGS

Embodiments of the invention will now be described with reference to the accompanying drawings in which.

DETAILED DESCRIPTION

Embodiments of the invention will now be described with reference to the drawings in which three embodiments are shown.

Figure 1:
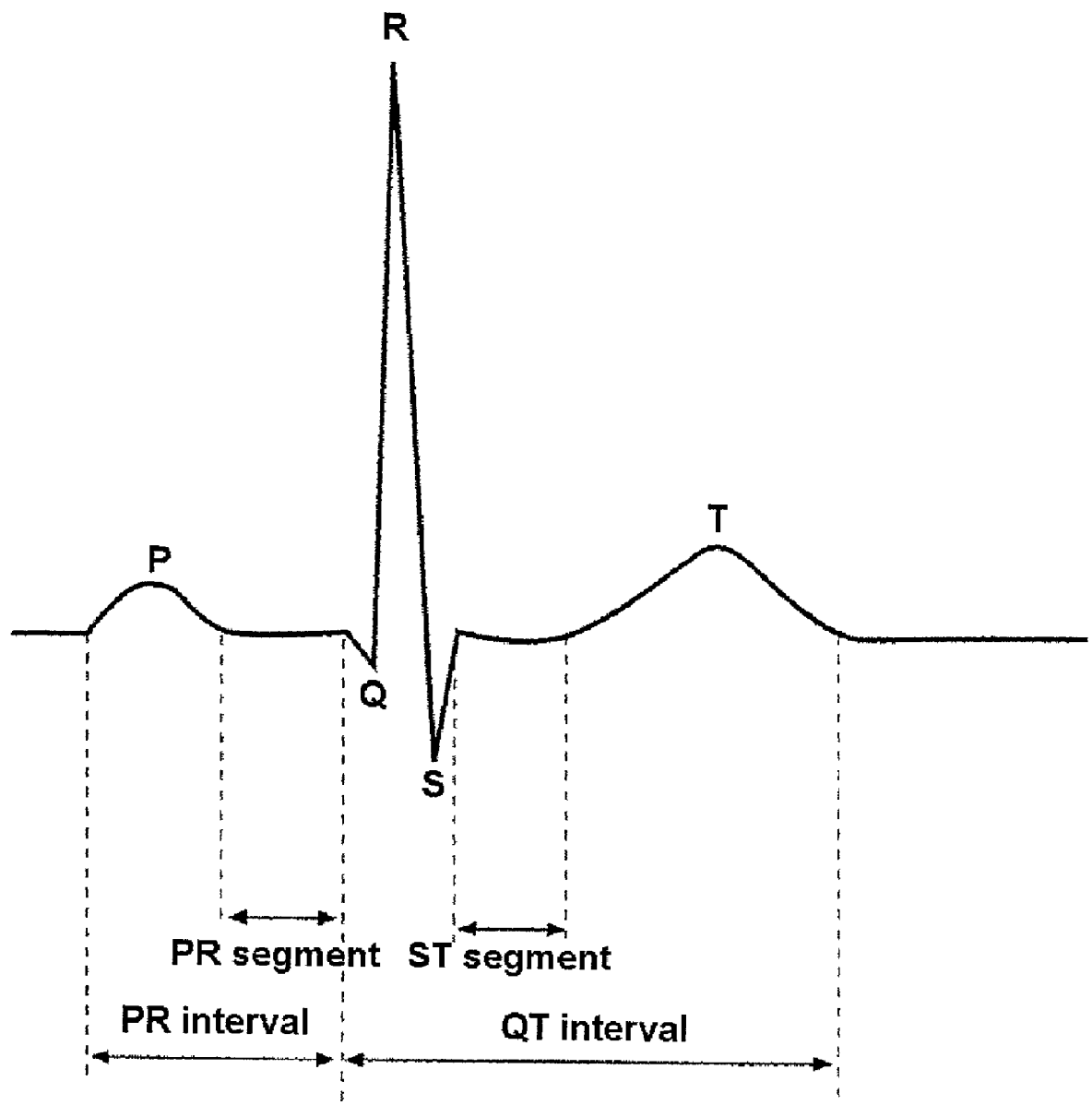
FIG. 1 is a diagram showing a typical electrocardiogram signal with the various intervals and segments identified.
Figure 2:
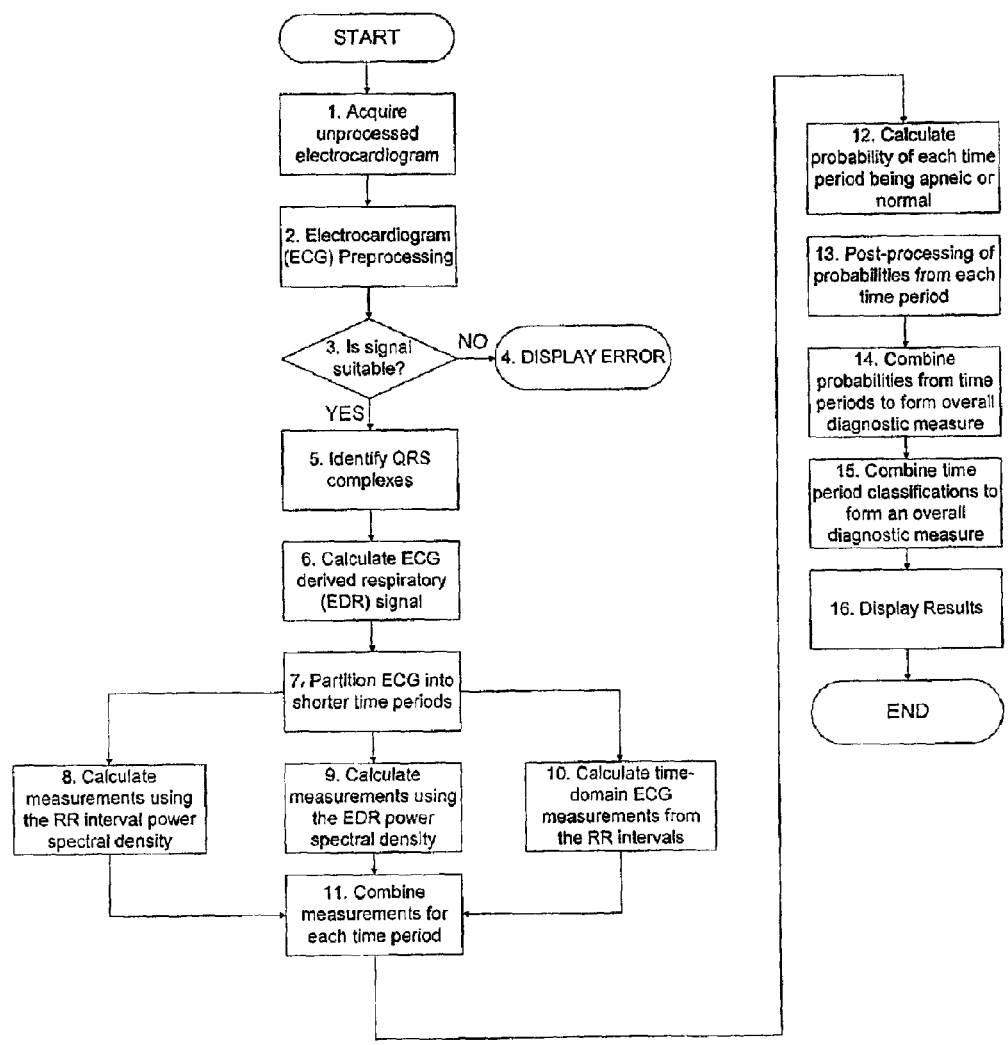
FIG. 2 is a flowchart setting out the steps involved in the method of the invention.

Referring initially to the flow chart of FIG. 2, the steps involved in the method of diagnosing sleep apnea in accordance with the present invention will now be described Step 1: Acquire Unprocessed Electrocardiogram Data:

A single channel electrocardiogram signal is acquired from a human using the diagnostic recording apparatus of the invention which incorporates a pair of differential electrodes. This is followed by amplification of the electrocardiogram signal, analogue anti-aliasing filtering, and analogue-to-digital signal conversion.

Step 2: Electrocardiogram Pre-processing

The unprocessed electrocardiogram signal acquired in Step 1 is corrupted by motion artifact, EMG noise, and powerline noise. Digital filtering techniques including a notch filter, lowpass filter, and median filter are employed to attenuate the effects of noise. The diagnostic recording apparatus includes signal processing circuitry to carry out such digital filtering techniques.

Step 3: Check if Electrocardiogram Signal is Suitable:

In exceptional circumstances, the filtered signal may still be unsuitable for further processing (e.g., too high a level of noise, or electrodes not connected). An algorithm such as examining the mean energy of the signal may be used to determine if a valid signal is being detected. If a signal is not being detected, then an error signal will be displayed on the diagnostic recording apparatus.

Step 4: Display Error if Signal is Deemed Unsuitable at Step 3:

Display error—a clear indicator will be visible (and may be audible) to indicate that the measured signal is not valid.

Step 5: Identify QRS Complexes:

The times of occurrences of the R-wave peak in the QRS complexes are determined. This stage of processing gives a series of times at which the R waves occur, and is used to determine the RR intervals.

Step 6: Calculate the ECG Derived Respiratory Signal

An electrocardiogram-derived respiratory signal is calculated by taking the locations of the R-wave peaks, and calculating the area represented by the signal near those locations.

Step 7: Partition ECG into Time Periods

The electrocardiogram is partitioned into a series of time periods. An example is the partitioning of the electrocardiogram into time periods of one minute duration.

Step 8: Calculate Measurements Using RR Interval Power Spectral Density:

The RR interval power spectral density is calculated from the RR intervals, using an averaged periodogram technique over the time periods of data.

Step 9: Calculate Measurements Using the Electrocardiogram Derived Respiratory Signal Power Spectral Density:

The power spectral density of the electrocardiogram-derived respiratory signal is calculated using the averaged periodogram technique over the time periods of data.

Step 10: Calculate Time Domain Electrocardiogram Measurements from the RR Intervals:

The following set of time domain measurements are calculated over the time periods of the RR intervals—they are more fully explained later: the mean RR interval, the standard deviation of the RR intervals, the first five serial correlation coefficients of the RR intervals, two variants of the value of NN50, two variants of the value of PNN50, the value of SDSD, the value of RMSSD, the value of the Allan factor at five different time scales, the mean electrocardiogram-derived respiratory signal amplitude, and the standard deviation of the electrocardiogram-derived respiratory signal amplitude. Global time domain measurements are also calculated from the entire recording. These are the mean and standard deviation of the RR intervals and the electrocardiogram-derived respiratory signal Step 11: Combine Measurements for Each Time Period:

The measurements from the RR interval power spectral density, the electrocardiogram-derived respiratory power spectral density, and the time domain electrocardiogram calculations obtained from steps 8, 9, and 10 for each time period are combined to be processed by step 11.

Step 12: Calculate Probability of Each Time Period Being Apneic or Normal:

The measurements from step 11 are processed by a classifier that has been trained on a pre-existing database of electrocardiogram signals. It calculates two probabilities for each time period. The first is the probability of one or more apneic episodes having occurred during that time period. The second is the probability of no apneic episodes having occurred during that time period. Note that the sum of the two probabilities is always one.

Step 13: Post-processing of Probabilities from Each Time Period:

The probability of each time period is recalculated by averaging it with the probabilities calculated from adjacent time periods. This introduces a time latency into the system.

Step 14: Classify Time Periods:

Each time period is assigned to either the normal or apneic class according to the class which has the higher probability from step 13.

Step 15: Combine Time Period Classifications to Form an Overall Diagnostic Measure:

The overall diagnostic measure is arrived at by combining the results of the time period classifications.

Step 16: Display Results of Classification:

The results for each time period and the overall diagnostic measure are displayed on a graphical interface, or in text form.

Example

The following is a more detailed description of the classification technique used in the invention, given by way of specific example. Electrocardiogram signals are obtained from a patient by using electrodes and analogue pre-amplifiers as in any standard Holter monitor. Suitable analogue amplification and filtering is implemented to provide a signal which is approximately band limited and within the range of the analog-to-digital converter. Preferably, the electrocardiogram signal is sampled at a rate of 100 Hz or higher, and at up to 16 bits per sample. The unprocessed signal is passed through a variety of digital filtering stages to provide bandpass filtering and removal of motion artifacts, powerline noise, and EMG noise.

A software algorithm to perform QRS detection is implemented. The software algorithm may be implemented on a computer, for example PC at a location remote from the recording apparatus. Alternatively, the software algorithm for QRS detection may be contained within the recording apparatus itself. This software algorithm provides the times at which the R-wave maximum occurs. The RR intervals are defined as the interval between R-wave peaks. This algorithm may provide some incorrect RR intervals. Data pre-processing steps to correct physiologically unreasonable RR intervals are carried out as follows:

Suspect RR intervals are found by applying a median filter of width five to the sequence of RR intervals. This provides a robust estimate of the expected value for each RR interval. Variations from this expected value lead to it being flagged as a suspect interval. Extraneous QRS detections are found by comparing the sum of adjacent RR intervals with the robust RR estimate. If this sum is numerically closer to the robust estimate than either of the individual RR intervals then an extraneous detection is present, and the two RR intervals are merged to form a single interval. Conversely, if an RR interval is a factor of 1.8 times or more than the robust estimate then it is probable that a QRS complex was not detected. To recover the missing QRS complexes the RR interval is divided by the sequence of integers 2, 3, 4, . . . until it best matches the robust estimate of the RR interval. The single RR interval is then subdivided by the appropriate integer to form a series of new detections. For each new detection, a search is made in region of 100 milliseconds either side of that detection for the maximum of the electrocardiogram signal. If this maximum is similar to the maxima of the surrounding QRS complexes, its time of occurrence is accepted as a valid QRS detection point, otherwise the original new detection point is used.

During the breathing cycle, the body-surface electrocardiogram is influenced by the electrode motion relative to the heart and by changes in thoracic electrical impedance as lungs fill and empty with air. The effect is most obviously seen as a slow modulation of the QRS amplitude at the same frequency as the breathing cycle. To access this signal, the unprocessed electrocardiogram signal is processed using a linear phase high pass filter with a cut-off frequency of 0.5 Hz to remove baseline wander. At every QRS detection time, a sample point of an electrocardiogram-derived respiratory signal is defined by calculating the area enclosed by the electrocardiogram in the region 50 ms before the R wave-maximum to 50 ms after The processing steps outlined above result in (1) a corrected set of RR intervals and (2) an electrocardiogram-derived respiratory signal derived from the R-wave amplitude for each one-minute time period. Based on these two signals derived from the electrocardiogram, a set of measurements is extracted which is then used for classifying whether a patient has sleep apnea or not and if so, the degree of sleep apnea.

The following measurements are obtained for each one-minute time period:

a) the power spectral density of the electrocardiogram-derived respiratory signal;

b) the mean and standard deviation of the electrocardiogram-derived respiratory signal;

c) the power spectral density of the RR-intervals;

d) the mean and standard deviation of the RR signal;

e) the first five serial correlation coefficients of the RR-intervals;

f) the Allan factor evaluated at a time scales of 5, 10, 15, 20 and 25 seconds where the Allan factor is defined as $$A(T) = \frac{E\{[N_{i+1}(T) - N_i(T)]^2\}}{2E\{N_{i+1}(T)\}},$$

and $N_i(T)$ is the number of R wave peaks occurring in a window of length T stretching from iT to (i+1)T;

g) the NN50 measure (variant 1), defined as number of pairs of adjacent RR intervals where the first interval exceeds the second interval by more than 50 ms;

h) the NN50 measure (variant 2), defined as number of pairs of adjacent RR intervals where the second interval exceeds the first interval by more than 50 ms;

i) two pNN50 measures, defined as the each NN50 measure divided by the total number of RR intervals;

j) the SDSD measures, defined as the standard deviation of the differences between adjacent RR intervals, and k) the RMSSD measure defined as the square root of the mean of the sum of the squares of differences between adjacent RR intervals.

All of the measurements (a)-(k) may be calculated over one minute of recording. In addition, four measurements are included for each minute by calculating the mean and standard deviation of the RR signal over the entire recorded electrocardiogram as well as the mean and standard deviation of the electrocardiogram-derived respiratory signal over the entire recorded electrocardiogram. Hence these four measurements are the same for all one-minute time periods of a recording.

The RR interval based power spectral density estimate is calculated in the following way. A sequence of RR intervals is associated with each one-minute time period. The index for this sequence is beat number, not time. The mean RR interval for that time period is removed from each value, to yield a zero-mean sequence. The sequence is zero-padded to length 256, and the fast Fourier transform is taken of the entire sequence. The squared amplitude of these transform values yield a periodogram estimate of the power spectral density, which has a high variance. Averaging of four adjacent frequency bins is used to yield a 64-point RR interval based power spectral density estimate (of which only bins 0-32 are relevant since bins 33-63 contain redundant measurements). The x-axis has units of cycles/beat (not Hz as for a rate-based power spectral density.

The electrocardiogram-derived respiratory spectrum is calculated as follows. For each record, the sequence of R-wave areas are calculated and a discrete sequence formed for each one-minute time period. The mean value for the block is removed prior to spectral estimation using the periodogram technique outlined above.

For each minute of recorded electrocardiogram, therefore an 88-element measurement vector x is created; vector x is composed of 32 separate frequency bins from the electrocardiogram-derived respiratory spectrum, and 32 separate frequency bins from the RR spectrum and the other measurements described above. This measurement vector is then used to classify the measured data into one of two classes: normal or apnea, using a linear discriminant classifier. In such a classifier, each measurement vector generates a set of K probability measures, where K is the number of possible classes (two in this case i.e. normal or apnea). The measure used is:

$$y_k = -\frac{1}{2}\mu_k^T \sum\nolimits^{-1} \mu_k + -\frac{1}{2}\mu_k^T \sum\nolimits^{-1} x + \log(p(k)), k = 1, 2,$$

where k denotes the class number, $\mu_k$ is the class mean, $\Sigma$ is the common covariance matrix, and p(k) is the a priori probability for that class. The class k which produces the highest value of $y_k$ is chosen as the correct class. The parameters $\mu_k$ and $\Sigma$ are chosen by a classifier training technique which is fully described in B. D. Ripley, "Pattern Recognition and Neural Networks" Cambridge University Press 1996. The linear discriminant classifier used in this disclosure was trained on a set of 35 records, each consisting of approximately 7-10 hours of electrocardiogram data. This equates to approximately 16000 minutes which have been classified as being either normal or apnea by an independent human expert. This classification is described in the Philipps University Sleep Apnea electrocardiogram database, available at http://physionet.org.

In addition, the classifications of each one-minute time period are not independent. It is possible to predict the classification of a one-minute time period based only on the classifications of the surrounding epochs with a success rate higher than that of random guessing. In light of this observation, the system and method of the present invention includes a technique to boost classification performance. To achieve this, the posterior probabilities of a time period are averaged with the posterior probabilities of the surrounding time periods. Another technique that may be used to boost classification performance is to average the measurement values over adjacent time periods before the classification stage.

Since the linear discriminant classifier provides a numerical estimate of the probability of apnea being present during a given one-minute time period, this knowledge can be used to assign a statistical confidence rating to each time period classification.

An unbiased estimate of expected classification performance using an additional 35 recordings not used in the training process says that our system will correctly classify 90.6% of one minute time periods. Factors which contribute to loss of accuracy are errors in the database "gold-standard" marking, data acquisition noise, and limitations in how well the measured data can actually capture the presence or absence of sleep apnea. As a comparative figure, it is estimated a highly skilled human observer using a polysomnogram would achieve an accuracy of around 93% on a per-minute basis.

The overall patient diagnosis is arrived at by combining the results of the minute-by-minute time periods. For example, if a person is found to have greater than 20% of their time being classified as apnea, then the overall record is denoted as apnea. Since the overall diagnosis combines information from many one-minute time periods, its accuracy is higher. On an independent data set of 30 clearly diagnosed patients available to the applicants, the diagnosis reached by using the apparatus, system, and method of the present invention, was in agreement with the clinician in all 30 cases.

There are three embodiments of the apparatus, system and method of diagnosing sleep apnea in accordance with this disclosure. These will now be described in turn.

Figure 3:
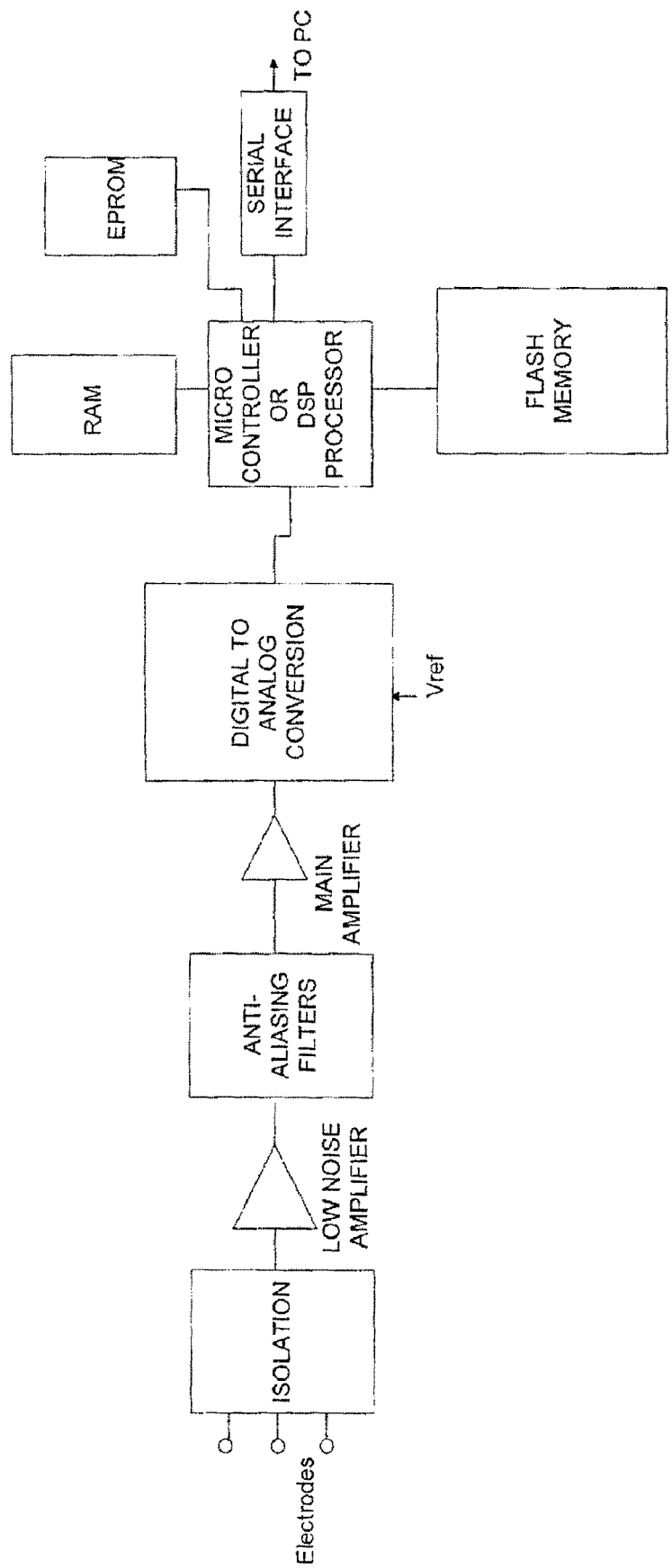
FIG. 3 is a schematic diagram of the diagnostic recorder electronic circuitry for the diagnostic recording apparatus in a first embodiment (PC-configuration embodiment)

Referring to FIGS. 3 to 6, the apparatus in the first embodiment, referred to as the PC-configuration, will be described. The apparatus in this first embodiment is indicated generally in FIG. 5 by the reference numeral 10. The apparatus 10 comprises a low noise amplifier, analogue filtering, analogue-to-digital conversion, digital filtering, digital memory including EPROM, random access memory (RAM), a microcontroller or DSP processor, and a high speed PC serial interface as indicated in FIG. 3. The apparatus also includes electrode inputs 11, a power indicator 12 and a PC interface port 13. The overall functionality of the diagnostic recording apparatus 10 is to provide a clean electrocardiogram signal that can be analyzed using the method of the invention described above.

The diagnostic recording apparatus is configured to accept differential inputs from several electrodes, giving one or more channels of electrocardiogram recording. The low noise amplifier provides initial amplification of the electrocardiogram signal. The anti-aliasing filter is required to allow digital sampling later in the circuit. This is followed by further amplification, and analogue-to-digital conversion. The controlling unit in the diagnostic recording apparatus is a microcontroller or DSP processor. The DSP processor may implement digital filtering to improve signal quality. The diagnostic recording apparatus 10 includes an EPROM to store its programming, random access memory (RAM) for intermediate calculations, and external flash memory to store the digital electrocardiogram data. The apparatus 10 also has a serial interface (such as a USB bus) that will allow it to communicate with an external computer since the analysis of the electrocardiogram recorded by the apparatus 10 is carried out on a computer at a location remote from apparatus 10.

The diagnostic recording apparatus may have the capability to record one or more channels of electrocardiogram signal. The recorder will store up to 24 hours of one or more channel recordings in a digital format using the flash memory indicated in the electronic circuitry diagram shown in FIG. 3. The diagnostic recording apparatus is lightweight, small in size, and battery powered and is rugged and light enough to be used on an outpatient basis (i.e., ambulatory).

Figure 4:
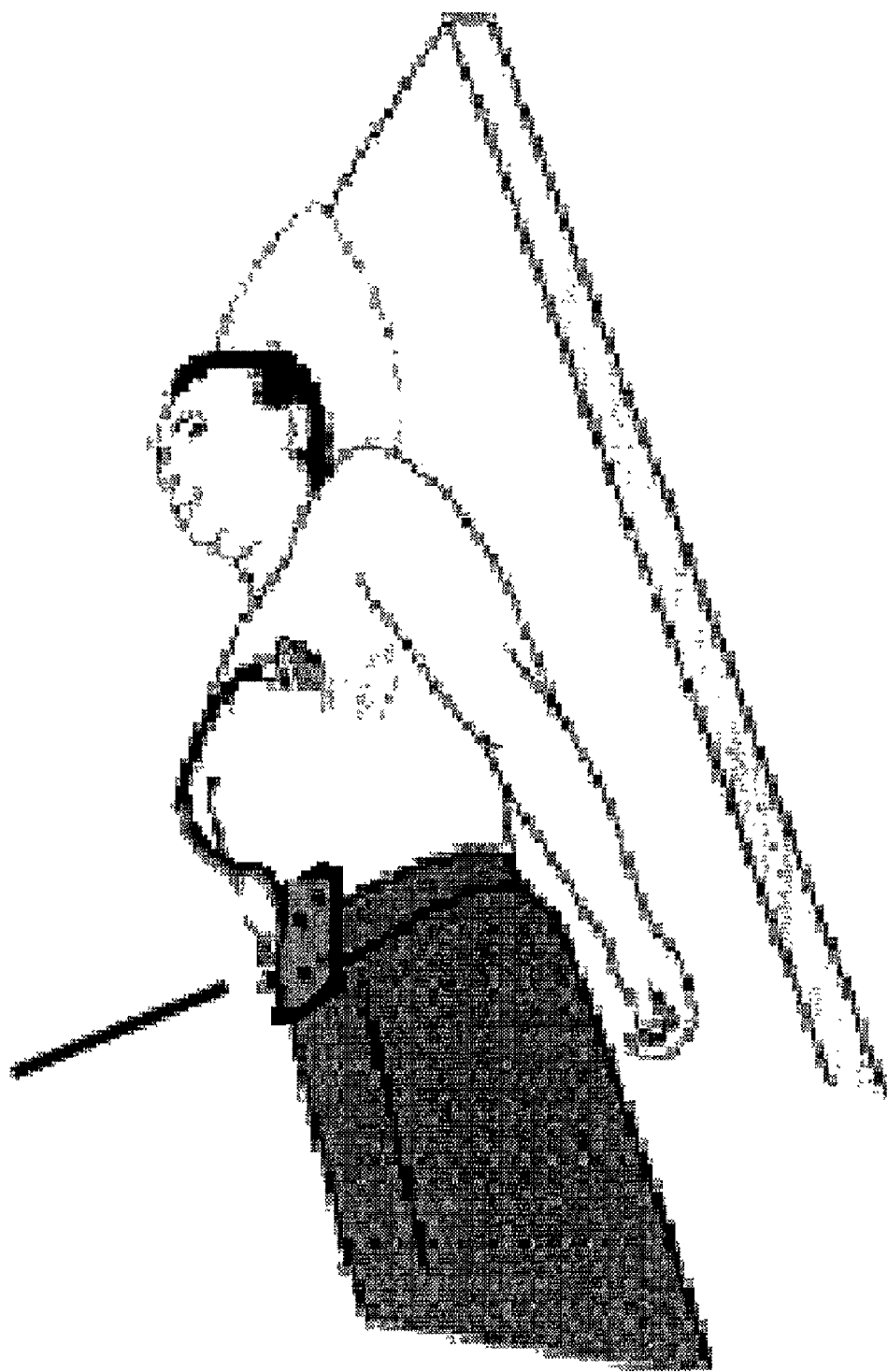
FIG. 4 is a diagram of a patient wearing the diagnostic recording apparatus while sleeping.

FIG. 4 shows how a patient can sleep while recording is occurring, with the recorder attached to the patient by means of a belt.

Figure 5:
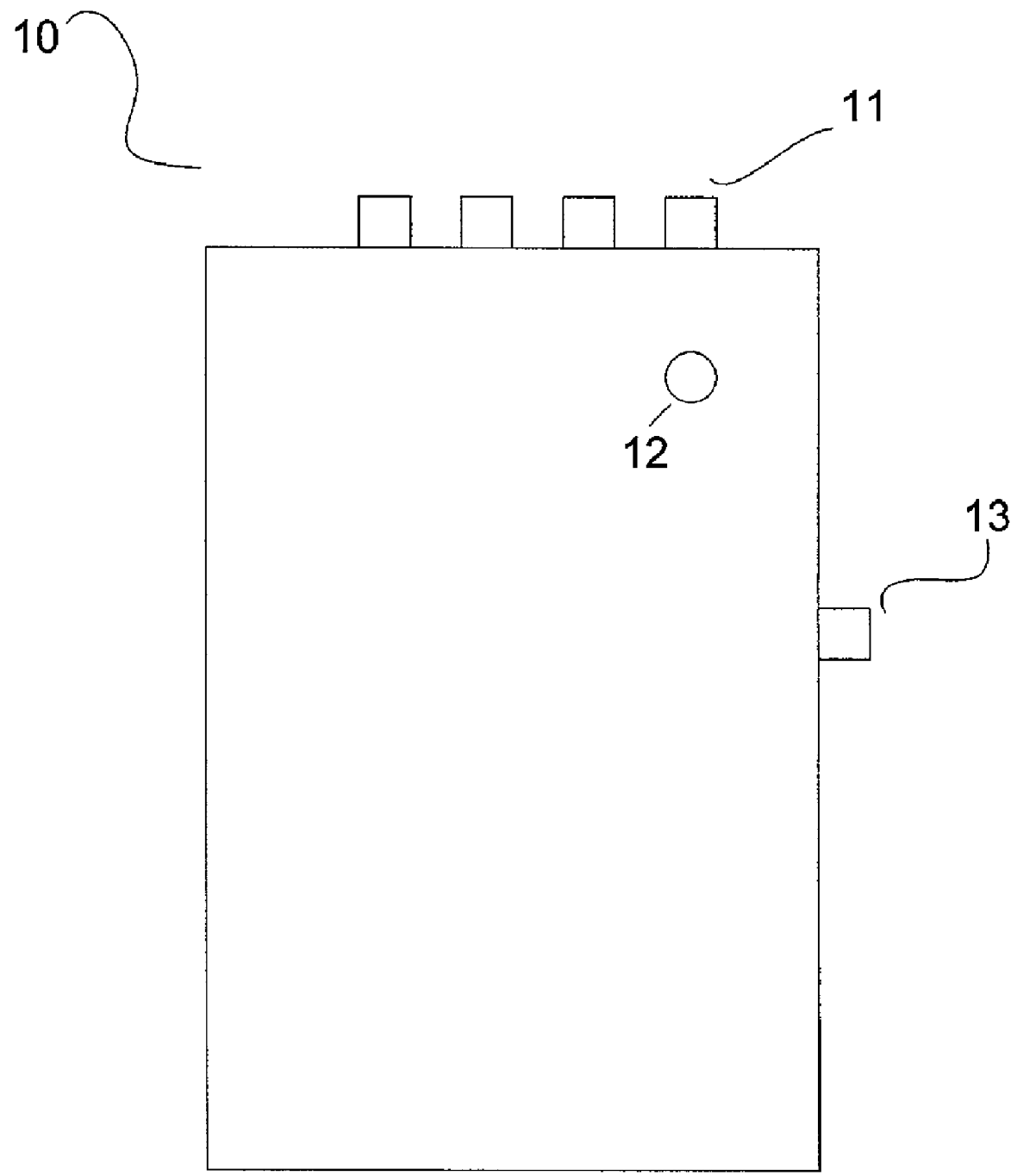
FIG. 5 is a schematic diagram of the features of the diagnostic recording apparatus in the first embodiment (PC-configuration embodiment)

FIG. 5 shows a sketch of the physical appearance of the diagnostic recording apparatus. The diagnostic recording apparatus 10 is small, measuring approximately 12 cm.times.8 cm and weighing about 150 g. The analysis carried out when implementing the method of this disclosure, described herein above as being implemented on a personal computer, which will also provide auxiliary functionality such as data archiving, database management, and compression.

Figure 6:
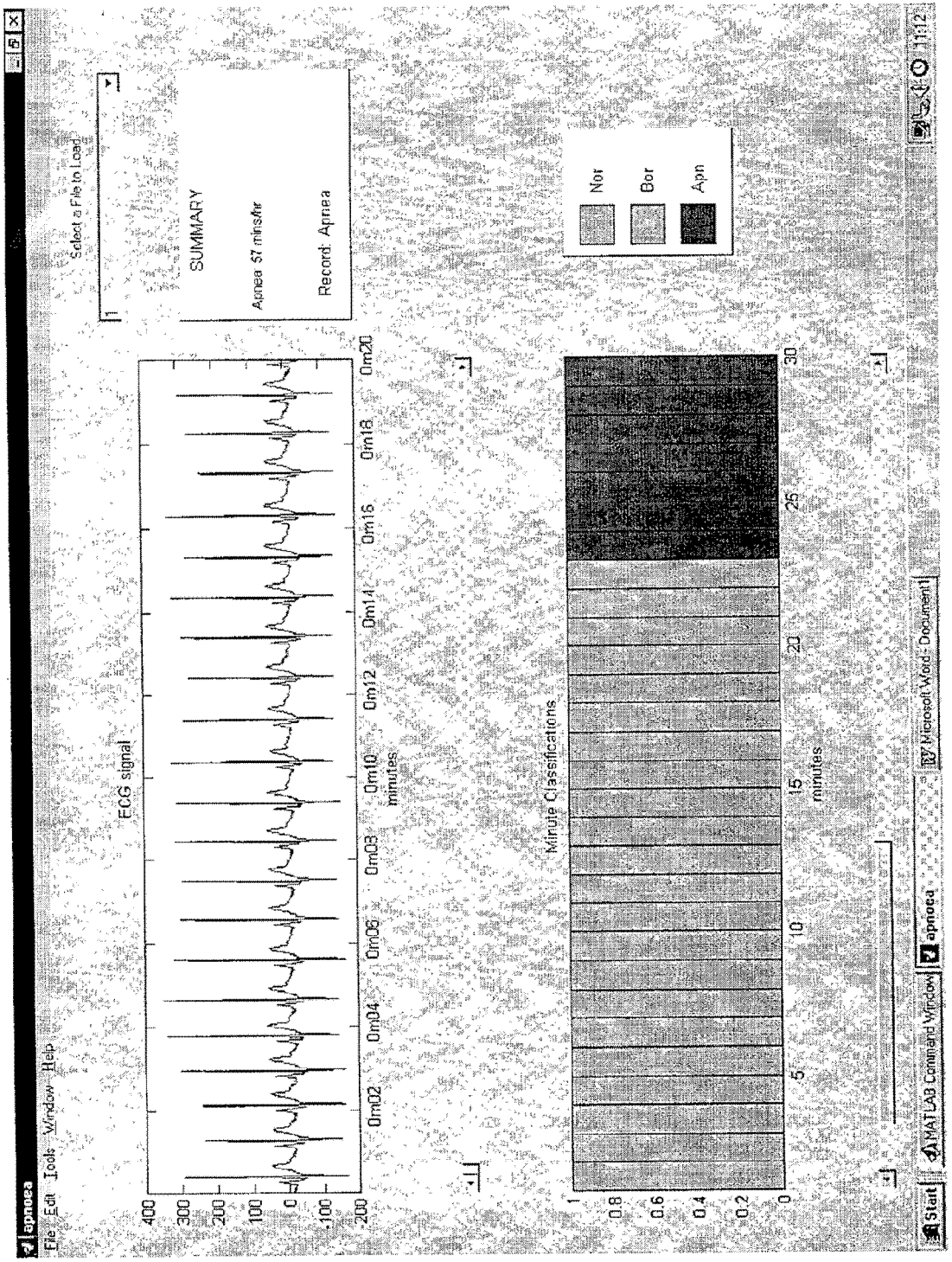
FIG. 6 is a diagram showing the analysis software interface on a PC in accordance with the first embodiment of the apparatus of the invention.

An embodiment of the analysis software interface is shown in FIG. 6. The interface details in graphic and text form the minute-by-minute breakdown of the electrocardiogram recording and apnea classification. It can use a simple color coding scheme (i.e. green for normal, red for apnea, orange for borderline) to provide an easy visual summary of the apnea activity. The interface can provide information such as the total number of apneic minutes, the percentage of apneic minutes, and an estimate of the apnea-hypopnea index (AHI).

The diagnostic recording apparatus 10 in this first embodiment is ideal for home monitoring, where the function of recording is separated from the function of analysis. The patient can be issued with the diagnostic recording apparatus, electrodes can be put in place, and the patient can return home to sleep. The following day (or at their own convenience), the patient can return the diagnostic recorder to the site where it was issued. Alternatively, in this embodiment, there may be a data link between the diagnostic recording apparatus 10 and the analysis system. The data acquired by the diagnostic recording apparatus may then be sent via a network to a separate physical location, and the analysis carried out at the remote location. This could be achieved by incorporating the functionality of a modem or wireless phone into the diagnostic recording apparatus, so that it can communicate with a computer located at the remote location. This has the advantage of providing a faster turn-around in analysis time.

Figure 7:
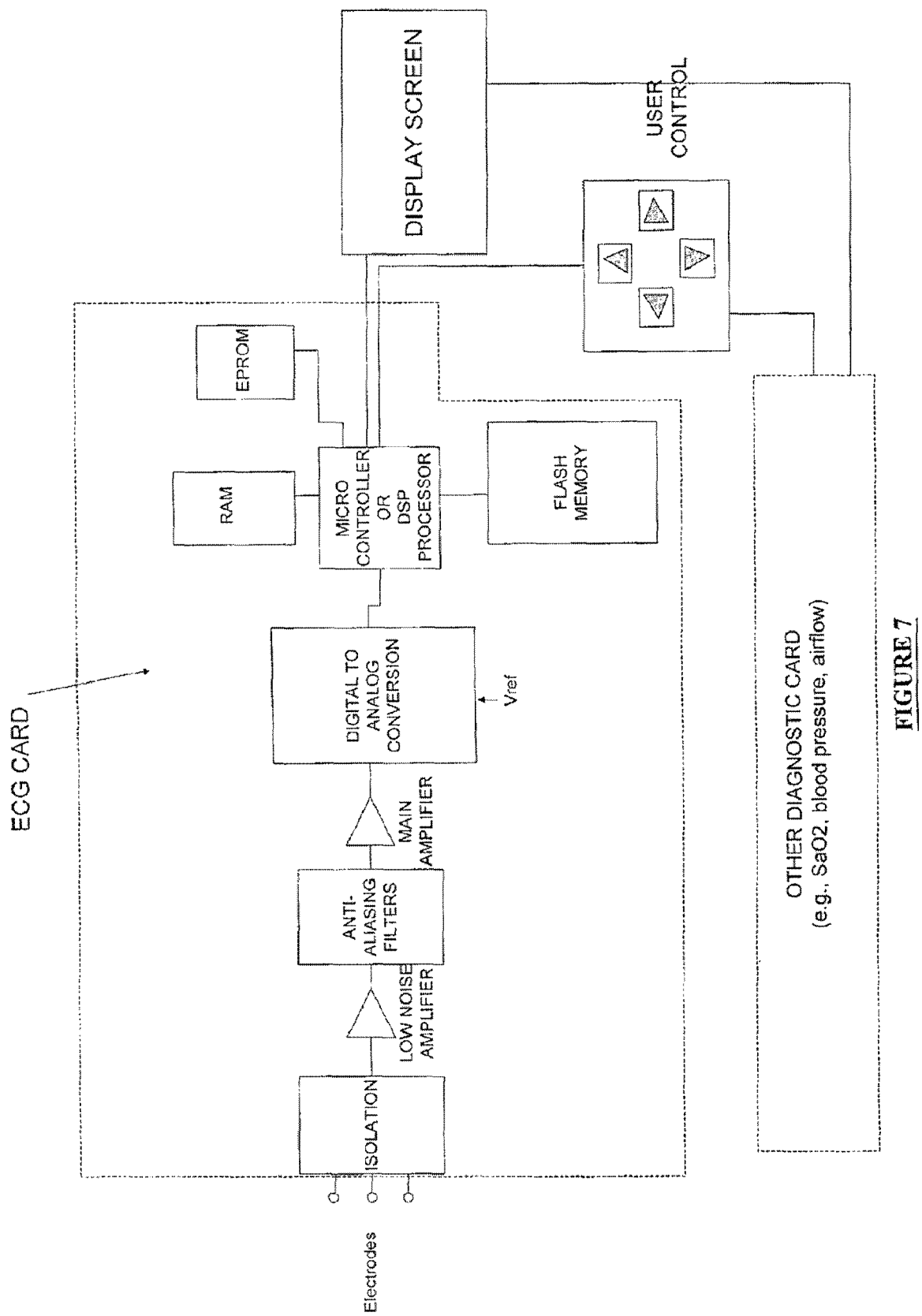
FIG. 7 is a schematic diagram of the electronic circuitry of the diagnostic recording apparatus in a second embodiment in which the data acquisition circuitry and analysis software is combined into a single unit (monitor-configuration embodiment)
Figure 8:
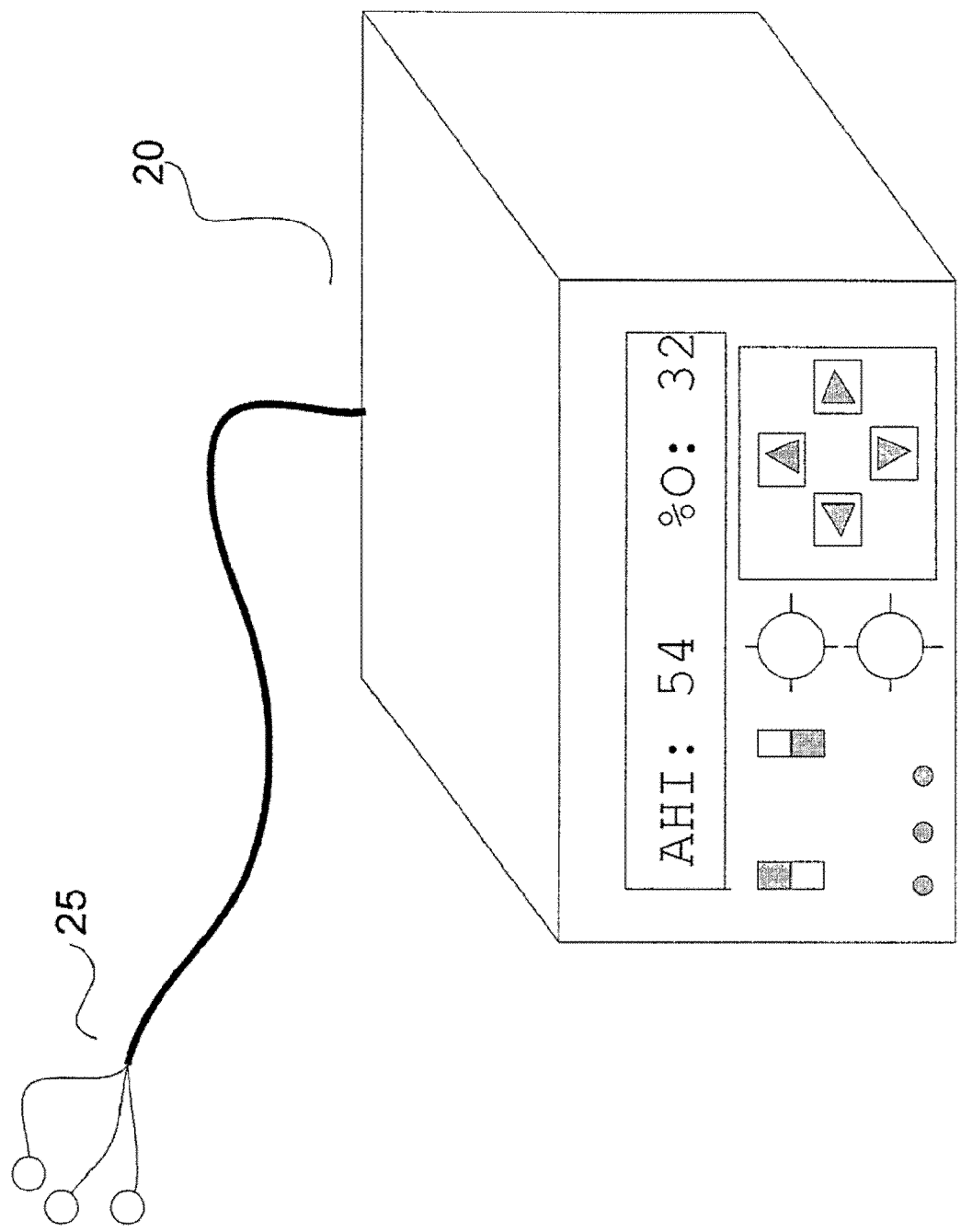
FIG. 8 is a perspective view of the apparatus in the second embodiment of the invention (monitor—configuration embodiment)

Referring now to FIGS. 7 and 8, the second embodiment of the diagnostic recording apparatus (referred to as monitor-configuration) is indicated generally by reference numeral 20 and this embodiment will now be described. The apparatus 20 incorporates the data acquisition circuitry including the low noise amplifier, analogue filtering, analogue-to-digital conversion, digital filtering, as well as the analysis software into a single physical unit. The diagnostic recording apparatus 20 also incorporates a user interface allowing the user to view the results of the analysis. The electrocardiogram electrodes 25 will be plugged directly into the diagnostic recording apparatus 20. The diagnostic recording apparatus 20 also contains a user display (labeled DISPLAY SCREEN in FIG. 7), and a simple user interface (i.e., simple back-forward buttons, labeled USER CONTROL in FIG. 7). The apparatus 20 could be used as a general-purpose monitoring unit to which other data acquisition cards may be attached (e.g., circuitry to measure nasal airflow, $SaO_2$, etc.). The diagnostic recording apparatus 20 is powered using mains supply. The apparatus 20 in this second embodiment is not intended to be ambulatory but rather is ideal for the situation where a subject is in a sleep laboratory or other medical facility.

Figure 9:
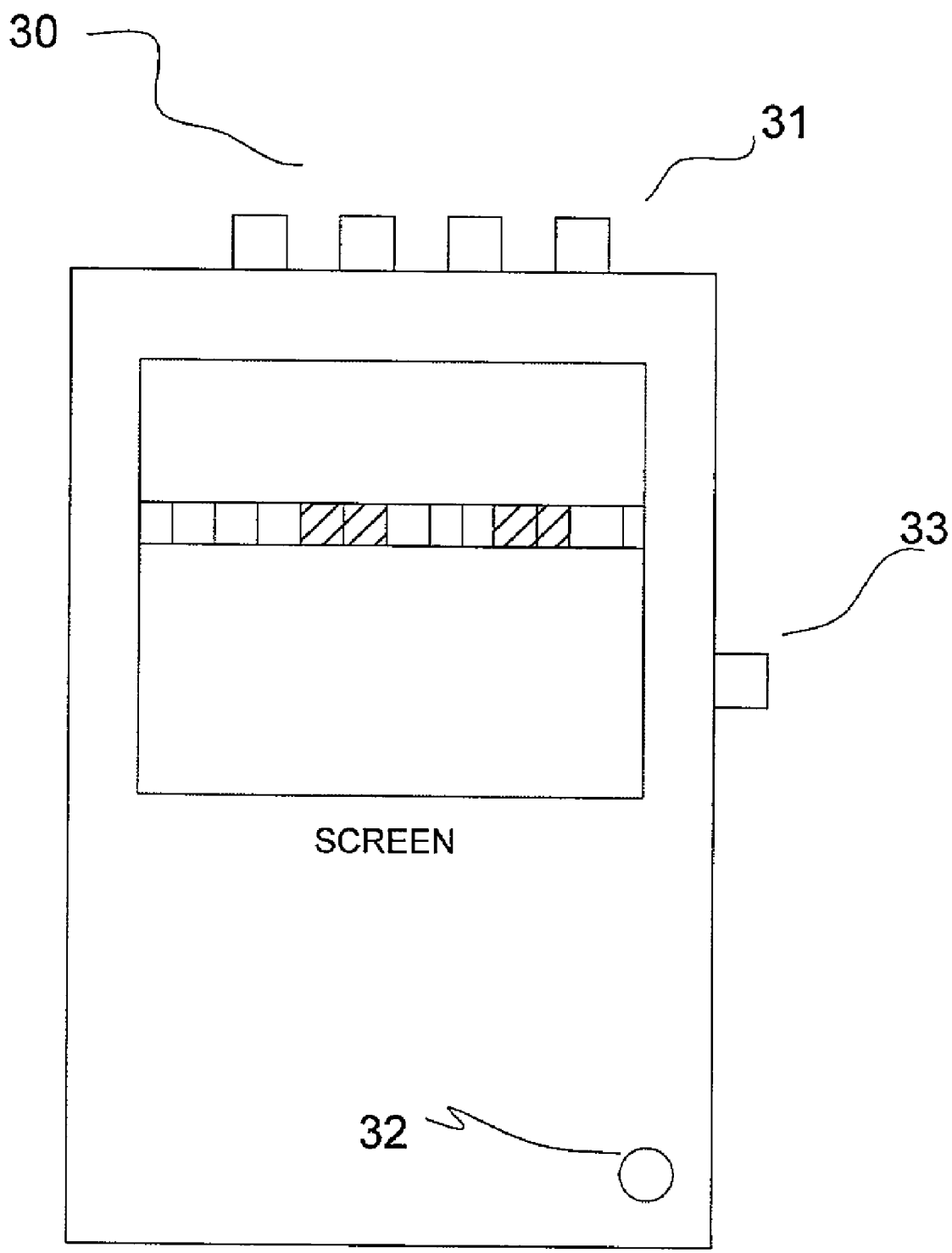
FIG. 9 is a schematic diagram of the apparatus in the third embodiment (stand-alone—configuration embodiment).

Referring now to FIG. 9, the diagnostic recording apparatus in a third embodiment (referred to as stand-alone-configuration) will be described. The apparatus in this embodiment is indicated generally by reference numeral 30. The apparatus 30 incorporates both the data acquisition and analysis software into a complete self-contained portable device. The apparatus 30 provides low noise amplification, analogue filtering, analogue-to-digital conversion, digital filtering, as well as providing the analysis. The apparatus 30 includes a simple user display (e.g. a small LCD screen), electrode inputs 31, power indicator 32 and serial interface 33. The device requires low-power, is low in weight, and battery operated and is also small (measuring approximately 12 cm.times.8 cm and weighing approximately 150 g). The apparatus 30 is suitable as a home healthcare consumer product, and can provide a summary of the night's sleep directly as output to a user. This might be ideal for patients who have undergone some treatment for sleep apnea, and who wish to monitor their progress.

In each of the above embodiments, measurements of additional physiological parameters such as $SaO_2$ level, respiratory effort, nasal airflow, body movement, etc. may be incorporated to enhance classification.

An advantage of the apparatus, system and method of this disclosure over conventional approaches in which 12 or more signals are often recorded, is that in the above-described simpler system, only one or two signals will be recorded using up to perhaps three electrical leads. This means that there are fewer body electrodes and measurement devices required. Furthermore, patient acceptance of skin electrodes on the chest is good, since such electrodes are comfortable, familiar and unobtrusive to sleeping for the general public.

The apparatus, method and system of this disclosure have the advantage that they provide diagnostic accuracy comparable with a complete polysomnogram, but at significantly reduced cost. The apparatus can also be embodied in a form suitable for home use, which lowers cost, and increases patient acceptance.

The apparatus, method and system of diagnosing sleep apnea in accordance with this disclosure has several advantages over conventional approaches. These at least include the following:

The apparatus and method rely upon use of the electrocardiogram signal only, rather than on the combination of electrocardiogram measurements with other signals such as $SaO_2$, sound, bodily position, etc.

The apparatus and method may incorporate a step to isolate an electrocardiogram-derived respiratory signal, which has useful diagnostic information. This has not previously been used to diagnose sleep apnea.

The apparatus and method may incorporate the use of spectral measures derived from the RR intervals and electrocardiogram-derived respiratory signal which have not been previously used to diagnose sleep apnea.

The apparatus and method may incorporate a large range of both time-domain and frequency-domain statistical measures of RR intervals which have not previously been used to diagnose sleep apnea The apparatus and method may incorporate post-processing of the time period classifications which increases the accuracy.

The apparatus and method may provide a diagnostic measure of sleep apnea for each time period. This is as compared to the Apnea-Hypopnea Index or Respiratory Disturbance Index currently used.

A further advantage is that the diagnostic recording apparatus can be made small and light enough to be worn comfortably while sleeping, and with sufficiently low power consumption to be powered by simple commercially available batteries.

A further advantage is that the device can be made small enough and easy to use at home allowing a simple screening protocol for sleep apnea to be implemented.

A further advantage is that the ambulatory diagnostic recording apparatus and diagnostic interpretation can be at two physically remote locations, allowing for remote monitoring and interpretation.

A further advantage of the system is that since the diagnostic recording apparatus records the electrocardiogram, it can provide useful information to other diagnostic systems, such as those monitoring for cardiac arrhythmias.

Thus, the apparatus, system and method disclosed above provides an inexpensive, highly-automated, diagnostic evaluation that has proven to be effective in classifying records from a known database of electrocardiogram signals. Tests on independent records show that the diagnostic accuracy on a per-minute basis is 90.6%, and on a per-patient basis is 100%.

It is to be understood that this disclosure has been particularly described with reference to single channel electrocardiograms, multi-channel electrocardiograms may equally be used in the apparatus, system and method of this disclosure.

It is thought that the various embodiments of the invention and its advantages will be understood from the foregoing description and it will be apparent that various changes may be made thereto without departing from the spirit and scope of the invention, the forms hereinbefore described being merely preferred or exemplary embodiments thereof.

What is claimed as new and desired to be protected by Letters Patent of the United States is:

1. An article of manufacture comprising a memory containing computer software program instructions therein which, when executed by a processor, cause the processor to:

analyze an electrocardiogram signal obtained from a human patient;

partition the electrocardiogram signal into a plurality of time periods;

derive an estimated respiration signal from the electrocardiogram signal;

classify each time period of the plurality of time periods of the electrocardiogram signal as either apneic or normal by analyzing both the electrocardiogram signal and the estimated respiration signal; and provide a diagnostic measure of sleep apnea for the human patient based on a combined classification result obtained by combining a plurality of the classifications from the plurality of time periods.

2. The article of manufacture of claim 1, wherein the computer software program instructions causes the processor to determine a plurality of R-R intervals in the electrocardiogram signal.

3. The article of manufacture of claim 1, wherein the computer software program instructions causes the processor to calculate a power spectral density of an RR interval.

4. The article of manufacture of claim 1, wherein the computer software program instructions causes the processor to determine the estimated respiration signal derived from the electrocardiogram signal, wherein the electrocardiogram signal is provided as a single lead electrocardiogram signal.

5. The article of manufacture of claim 4, wherein the computer software program instructions causes the processor to calculate a power spectral density of the estimated respiration signal.

6. The article of manufacture of claim 1, wherein the computer software program instructions causes the processor to use time domain processing to provide the diagnostic measure of sleep apnea.

7. The article of manufacture of claim 1, wherein the computer software program instructions causes the processor to use frequency domain processing to provide the diagnostic measure of sleep apnea.

8. The article of manufacture of claim 1, wherein the computer software program instructions causes the processor to use both time domain and frequency domain processing to provide the diagnostic measure of sleep apnea.

9. The article of manufacture of claim 1, wherein the computer software program instructions causes the processor to calculate, for each time period in the plurality of times periods, an associated probability that each of the plurality of time periods is apneic.

* * * * *